United States Patent [19]

Carr et al.

[11] 4,180,583
[45] Dec. 25, 1979

[54] OLEFINIC 4-SUBSTITUTED PIPERIDINO DERIVATIVES AS THERAPEUTICS

[75] Inventors: Albert A. Carr, Cincinnati; C. Richard Kinsolving, Terrace Park, both of Ohio

[73] Assignee: Richardson-Merrell Inc., Wilton, Conn.

[21] Appl. No.: 892,636

[22] Filed: Apr. 3, 1978

Related U.S. Application Data

[60] Division of Ser. No. 538,504, Jan. 6, 1975, abandoned, which is a continuation of Ser. No. 221,820, Jan. 28, 1972, Pat. No. 3,862,173.

[51] Int. Cl.² ............... A61K 27/00; A61K 31/40; A61K 31/445; A61K 31/495
[52] U.S. Cl. ............................. 424/267; 424/248.4; 424/250; 424/274
[58] Field of Search ............ 424/267, 250, 274, 248.4

[56] References Cited

U.S. PATENT DOCUMENTS

| | | | |
|---|---|---|---|
| 2,739,968 | 3/1956 | Sperber et al. | 260/293 |
| 3,068,237 | 12/1962 | Rorig | 260/294.7 |
| 3,423,406 | 1/1969 | Mull et al. | 260/240 |
| 3,734,924 | 5/1973 | Black et al. | 260/309 |
| 3,736,331 | 5/1973 | Black et al. | 260/309 |
| 3,759,928 | 9/1973 | Zirskovic | 260/293.72 |

OTHER PUBLICATIONS

Goodman et al., "The Pharmacological Basis of Therapeutics", p. 638, (1970).

*Primary Examiner*—Stanley J. Friedman
*Attorney, Agent, or Firm*—L. Ruth Hattan; Eugene O. Retter; George W. Rauchfuss, Jr.

[57] ABSTRACT

Novel compounds useful as antihistamine agents, antiallergy agents, and bronchodilators are represented by the following formula

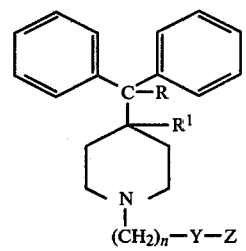

wherein R and R¹ each represent hydrogen; or R and R¹ taken together form a second bond between the carbon atoms bearing R and R¹; n is a positive whole integer of from 1 to 3; Y represents —CH=CH—, or

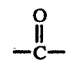

with the proviso that when each of R and R¹ represents hydrogen, Y represents —CH=CH, and when Y represents —CH=CH, n is equal to 1 or 2; and Z represents thienyl, phenyl, or substituted phenyl wherein the substituents on the substituted phenyl may be attached at the ortho, meta, or para positions of the phenyl ring and are selected from halogen, a straight or branched lower alkyl chain of from 1 to 4 carbon atoms, a lower alkoxy group of from 1 to 4 carbon atoms, di(lower)-alkylamino, or a saturated monocyclic heterocyclic group such as pyrrolidino, piperidino, morpholino, or N-(lower)-alkylpiperazino. Pharmaceutically acceptable acid addition salts and individual geometric isomers of compounds of the above formula are also included as a part of this invention.

12 Claims, No Drawings

OLEFINIC 4-SUBSTITUTED PIPERIDINO DERIVATIVES AS THERAPEUTICS

FIELD OF INVENTION

This is a division, of application Ser. No. 538,504, filed Jan. 6, 1975, now abandoned, which is a continuation of application Ser. No. 221,820, filed Jan. 28, 1972, now U.S. Pat. No. 3,862,173 issued Jan. 21, 1975.

This invention relates to novel olefinic 4-substituted piperidine derivatives. More particularly this invention relates to 4-diphenylmethyl- and 4-diphenylmethylenepiperidino derivatives which are useful as antihistamines, antiallergy agents and bronchodilators and to methods of making and using the same.

SUMMARY OF INVENTION

The novel olefinic 4-substituted piperidine derivatives of this invention useful as antihistamines, antiallergy agents, and bronchodilators are represented by the formula

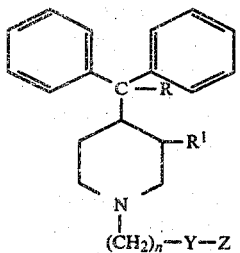

Formula I wherein R and $R^1$ each represent hydrogen; or R and $R^1$ taken together form a second bond between the carbon atoms bearing R and $R^1$; n is a positive whole integer of from 1 to 3; Y represents —CH=CH—, or

with the proviso that when each of R and $R^1$ represents hydrogen, Y represents —CH=CH—, and when Y represents —CH=CH—, n is equal to 1 or 2; and Z represents thienyl, phenyl or substituted phenyl wherein the substituents on the substituted phenyl are selected from an halogen atom, such as chlorine, fluorine, bromine, or iodine, a straight or branched lower alkyl chain of from 1 to 4 carbon atoms, a lower alkoxy group of from 1 to 4 carbon atoms, a di(lower)alkylamino group, or a saturated monocyclic heterocyclic group such as pyrrolidino, piperidino, morpholino, and N-(lower)alkylpiperazino and may be attached at the ortho, meta, or para positions of the phenyl ring. Included in the scope of this invention are the pharmaceutically acceptable acid addition salts and individual geometric isomers of the compounds of Formula I.

DETAILED DESCRIPTION OF INVENTION

It can be seen from the above Formula 1 that compounds of this invention may be 4-diphenylmethyl-piperidine derivatives as represented by the following Formula II, or 4-diphenylmethylenepiperidine derivatives as represented by the following Formula III.

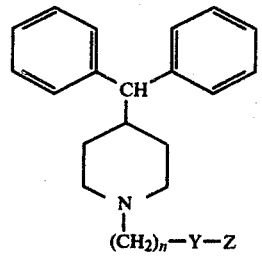

Formula II

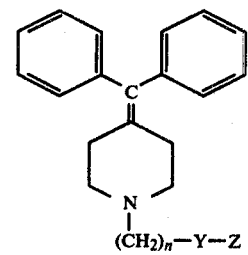

Formula III

In the above Formula II and III, n, Y, and Z have the same meanings as defined hereinbefore.

The term lower alkyl as used in describing the compounds of this invention is taken to mean a straight or branched alkyl chain of from 1 to 4 carbon atoms. As examples of lower alkyl groups that may be present in the compounds of Formulas I to III as a straight or branched lower alkyl substituent, or in the di(lower)alkylamine substituent, or in the N-(lower)alkylpiperazine substituent on Z when Z represents a substituted phenyl there may be mentioned, methyl, ethyl, n-propyl, n-butyl, isopropyl, isobutyl and tert-butyl.

A preferred group of compounds of this invention are those of general Formulas II and III wherein Y represents —CH=CH— and n is equal to 2 as represented by the following general Formula IV.

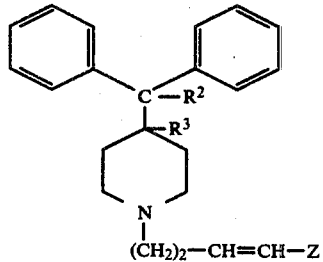

Formula IV

In the above general formula IV, $R^2$ and $R^3$ each represent hydrogen, or $R^2$ and $R^3$ taken together form a second bond between the carbon atoms bearing $R^2$ and $R^3$, and Z has the meaning defined hereinbefore.

Another preferred group of compounds of this invention are those of general Formula III wherein Y represents

and n is equal to 3 as represented by the following general Formula V.

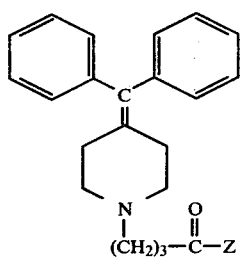

Formula V

In the above general Formula V, Z has the meaning defined hereinbefore.

This invention also includes the pharmaceutically acceptable acid addition salts of the compounds of the hereinbefore set forth formulas, geometric isomers and salts thereof. Pharmaceutically acceptable acid addition salts of the compounds of this invention are those of any suitable inorganic or organic acid. Suitable inorganic acids are, for example, hydrochloric, hydrobromic, sulphuric, phosphoric acids and the like. Suitable organic acids include carboxylic acids such as, for example, acetic, propionic, glycolic, lactic, pyruvic, malonic, succinic, fumaric, malic, tartaric, citric, ascorbic, maleic, hydroxymaleic, and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic acid and the like, sulfonic acids such as, for example, methanesulfonic, ethanesulfonic, β-hydroxyethanesulfonic acid, and the like.

As examples of compounds illustrative of this invention there may be mentioned, for example, 4'-fluoro-4-(4-diphenylmethylenepiperidino)butyrophenone, 3-[4-(diphenylmethylene)-1-piperidyl]-1-(2-thienyl)-1-propanone, 4-(4-diphenylmethylenepiperidino)butyrophenone, 1-(4-phenyl-3-butenyl)-4-diphenylmethylpiperidine, 1-[4-(p-fluorophenyl)-3-butenyl]-4-diphenylmethylpiperidine, 1-[3-(p-tolyl)-2-propenyl]-4-diphenylmethylpiperidine, 4'-tert-butyl-4-(4-diphenylmethylenepiperidino)butyrophenone, 1-[4-(p-dimethylaminophenyl)-3-butenyl]-4-diphenylmethylenepiperidine, 1-[4-(p-isopropylphenyl)-3-butenyl]-4-diphenylmethylenepiperidine, 1-[3-(p-fluorophenyl)-2-propenyl]-4-diphenylmethylenepiperidine, 4'-methoxy-4-(4-diphenylmethylenepiperidino)butyrophenone, and the like.

The novel compounds of this invention are useful as antihistamines, antiallergy agents and bronchodilators and may be administered alone or with suitable pharmaceutical carriers, and can be in solid or liquid form such as, for example, tablets, capsules, powders, solutions, suspensions, or emulsions.

The compounds of this invention can be administered orally, parenterally, for example, subcutaneously, intravenously, intramuscularly, intraperitoneally, by intranasal instillation or by application to mucous membranes such as that of the nose, throat, and bronchial tubes, for example, in an aerosol spray containing small particles of a compound of this invention in a spray or dry powder form.

The quantity of novel compound administered will vary. Depending on the patient and the mode of administration, the quantity of novel compound administered may vary over a wide range to provide in a unit dosage of from about 0.01 to 20 milligrams per kilogram of body weight of the patient per dose to achieve the desired effect. For example the desired antihistamine, antiallergy and bronchodilator effects can be obtained by consumption of a unit dosage form such as, for example, a tablet containing 1 to 50 milligrams of a novel compound of this invention taken 1 to 4 times daily.

The solid unit dosage forms can be of the conventional type. Thus, the solid form can be a capsule which can be of the ordinary gelatin type containing a novel compound of this invention and a carrier, for example, lubricant and inert fillers such as lactose, sucrose, corn starch, and the like. In another embodiment, the novel compounds are tabletted with conventional tablet bases such as lactose, sucrose, corn starch, and the like in combination with binders such as acacia, corn starch or gelatin, disintegrating agents such as corn starch, potato starch, or alginic acid, and a lubricant such as stearic acid, or magnesium stearate.

The novel compounds may also be administered as injectable dosages by solution or suspension of the compounds in a physiologically acceptable diluent with a pharmaceutical carrier which can be a sterile liquid such as water and oils, with or without the addition of a surfactant and other pharmaceutically acceptable adjuvants. Illustrative of oils there can be mentioned those of petroleum, animal, vegetable or synthetic origin, for example, peanut oil, soybean oil, mineral oil, and the like. In general, water, saline, aqueous dextrose, and related sugar solutions, and ethanols and glycols such as propylene glycol or polyethylene glycol are preferred liquid carriers, particularly for injectable solutions.

For use as aerosols the novel compounds in solution or suspension may be packaged in a pressurized aerosol container together with a gaseous or liquefied propellant, for example, dichlorodifluoromethane, dichlorodifluoromethane with dichlorodifluoroethane, carbon dioxide, nitrogen, propane, etc. with the usual adjuvants such as cosolvents, and wetting agents, as may be necessary or desirable. The compounds may also be administered in a non-pressurized form such as in a nebulizer or atomizer.

To illustrate the utility of the compounds of this invention the following tabulation indicates the amount of certain representative compounds of this invention required to reduce by 50% wheals induced by intradermal injections of 1γ each of histamine into guinea pigs. Each compound was orally administered one hour prior to the histamine injection.

| Ex. no. | Compound | ED$_{50}$ mg/kg |
| --- | --- | --- |
| 2 | 4-(Diphenylmethyl)-1-[4-(p-fluorophenyl)-3-butenyl]-piperidine hydrochloride hemihydrate | 14.4 |
| 5 | 4-[4-(Diphenylmethylene)-piperidino]-1-(2-thienyl)-1-butanone hydrochloride | 3.1 |
| 9 | 4'-tert-Butyl-4-[4-diphenylmethylene)piperidino]butyrophenone | 4.0 |

The minimal amounts of the compounds of Examples 5 and 9 required to prevent aerosol antigen induced bronchial spasms and death in the guinea pig are respectively 4.0 and 8.0 milligrams per kilogram of body weight orally.

The example numbers of the above mentioned compounds correspond to the example numbers of the specific examples of compounds used to illustrate the invention.

The compounds of this invention may be prepared by an acid catalyzed dehydration of the corresponding hydroxy containing derivative as indicated by the following reaction.

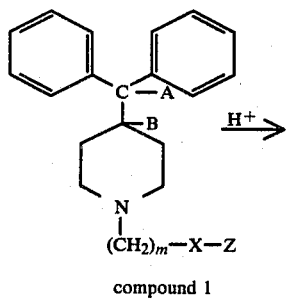

compound 1

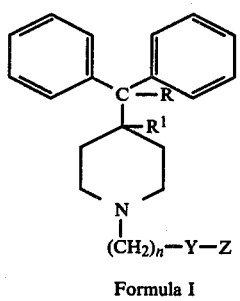

Formula I

In the above reaction Z has the meaning defined hereinbefore; A represents hydrogen or hydroxy; B represents hydrogen; or A and B together form a second bond between the carbon atoms bearing A and B; X represents

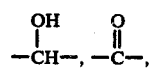

or —CH=CH—; m is an integer of from 1 to 3 with the proviso that when each of A and B represents hydrogen, or when A and B together form a second bond, X represents

and with the proviso that when X represents

m is equal to 2 or 3, and with the proviso that when X represents —CH=CH—, m is equal to 1, A represents hydroxy, and B represents hydrogen; R and R¹ each represent hydrogen; or R and R¹ together form a second bond between the carbon atoms bearing R and R¹; n is an integer of from 1 to 3; and Y represents

or —CH=CH— with the proviso that when each of R and R¹ represents hydrogen, Y represents —CH=CH—, and when Y represents —CH=CH—, n is equal to 1 or 2.

In the above reaction the starting materials as represented by compound 1 may be used as the free base or as the corresponding acid addition salt. Suitable acids for this dehydration reaction include hydrochloric acid, hydrobromic acid, phosphoric acid, and the like. Acetic acid may be used in combination with either the hydrochloric or hydrobromic acid also. The reaction is carried out in solvents such as water, methyl isobutyl ketone, methanol, ethanol, isopropyl alcohol, n-butanol, acetic acid and the like for from about 1 to 120 hours at temperatures varying from about 50° to 150° C. Generally the reaction temperature is about 100° C.

The α-aryl-4-(α-hydroxy-α-phenylbenzyl)-, the α-aryl-4-(diphenylmethyl)- and the 4-(diphenylmethylene)piperidinoalkanol reactants, that is, compound 1 wherein X represents

and A, B, m, and Z have the meanings defined hereinabove, may be obtained by reducing the corresponding 4-substituted piperidinoalkanone derivative, or by an alkylation reaction of 4-(α-hydroxy-α-phenylbenzyl)-piperidine, 4-(diphenylmethyl)piperidine, or 4-(diphenylmethylene)-piperidine with an appropriate α-aryl ω-haloalkanol compound as disclosed in copending application Ser. No. 221,821 abandoned and refiled as Ser. No. 378,561 now U.S. Pat. No. 3,878,217 issued Apr. 15, 1975, incorporated herein by reference thereto.

The aryl 4-[4-(α-hydroxy-α-phenylbenzyl)-]piperidinoalkyl ketone reactants, that is, compound 1 wherein A represents OH, B represents H, m is an integer of from 1 to 3, X represents

and Z has the meaning defined hereinbefore may be obtained by an alkylation reaction of α,α-diphenyl-4-piperidinemethanol with an appropriate aryl ω-haloalkyl ketone.

The olefinic N-substituted-α,α-diphenyl-4-piperidinemethanol reactants, that is, compound 1 wherein A represents hydroxy, B represents hydrogen, m is the integer 1, X represents —CH=CH—, and Z has the meaning defined hereinbefore may be obtained by the alkylation of α,α-diphenyl-4-piperidinemethanol with a 1-aryl-3-halo-1-propenyl compound.

The compounds of Formula I wherein R and R¹ together form a second bond, n is an integer of from 1 to 3, and Y represents

may also be prepared by alkylating 4-(diphenylmethylene)piperidine with an aryl ω-haloalkyl ketone. Similarly, the compounds of Formula I wherein each of R and R¹ represent hydrogen, or R and R¹ form a second bond, n is the integer 1, and Y represents —CH=CH— may be prepared by the alkylation of an appropriately substituted piperidine compound with a 1-aryl-3-halo-1-propenyl compound.

The above mentioned alkylation reactions are carried out in alcoholic solvents such as methanol, ethanol, isopropyl alcohol, n-butanol, and the like, in ketone solvents such as methyl isobutyl ketone, and the like, in hydrocarbon solvents such as benzene, toluene, and the like, or in halogenated hydrocarbons, such as chlorobenzene, and the like, in the presence of an inorganic base such as sodium bicarbonate, potassium carbonate, and the like, or in the presence of an organic base such as triethylamine or an excess of an piperidine derivative starting material. In some cases it may be desirable to add catalytic amounts of potassium iodide to the reaction mixture. The reaction time is usually about 48 hours, but may vary from about 4 to 120 hours at a temperature of from about 70° C. to the reflux temperature of the solvent.

The following specific examples are illustrative of the invention.

EXAMPLE 1

1-(4-Phenyl-3-butenyl)-4-(diphenylmethyl)piperidine hydrochloride

A mixture of 4-(diphenylmethyl)-α-phenyl-1-piperidinebutanol and 400 ml of 37% HCl was refluxed for 16 hours after which the solvent was removed at reduced pressure. The remaining residue was dissolved in 1 liter of toluene, treated with charcoal and filtered. The filtrate was concentrated to 500 ml, and a solid formed which was recrystallized from butanone and toluene to give the desired product, M.P. 188.5°-209° C.

EXAMPLE 2

4-(Diphenylmethyl)-1-[4-(p-fluorophenyl)-3-butenyl]-piperidine hydrochloride hemihydrate A mixture of 24 g (0.057 mole) of 4-(diphenylmethyl)-α-(p-fluorophenyl)-1-piperidinebutanol, 500 ml of 37% HCl, 100 ml of butanone and 200 ml of isopropyl alcohol was heated to reflux under an atmosphere of nitrogen for 18 hours. The solvent and excess acid were removed under vacuum and the residue was dissolved in toluene. Ether was added to the toluene solution, and an oily precipitate formed. The toluene and ether were decanted, and the precipitate was recrystallized from ethyl acetate to give the desired product, M.P. 143°-148° C.

EXAMPLE 3

4-[4-(Diphenylmethylene)piperidino]-4'-fluorobutyrophenone hydrochloride

A mixture of 17.7 g (0.038 mole) of 4'-fluoro-4-[4-(α-hydroxy-α-phenylbenzyl)piperidino]butyrophenone hydrochloride, 200 ml of 37% HCl, and 200 ml of isopropyl alcohol was heated on a steam bath for 4 hours. The solvent and excess acid were removed at reduced pressure. The remaining residue was treated with benzene and ethanol and heated to remove excess acid. The excess benzene and ethanol were removed, and the residue was dissolved in hot butanone to which ether was added. Upon cooling a solid formed which was recrystallized from ethyl acetate to give the desired product M.P. 190°-191° C.

EXAMPLE 4

4-Diphenylmethylene-1-[4-(p-fluorophenyl)-3-butenyl]-piperidine hydrochloride

A mixture of 15 g (0.034 mole) of α-(p-fluorophenyl)-4-(α-hydroxy-α-phenylbenzyl)-1-piperidinebutanol, 400 ml of concentrated HCl and 1500 ml of isopropyl alcohol was heated on a steam bath for 16 hours. The isopropyl alcohol was then concentrated by heating, and the remaining solution was cooled to room temperature. A precipitate formed which was collected on a filter and recrystallized from isopropyl alcohol and ethyl acetate to give the desired product, M.P. 166°-168.5° C.

EXAMPLE 5

4-[4-(Diphenylmethylene)piperidino]-1-(2-thienyl)-1-butanone hydrochloride

A mixture of 22.8 g (0.05 mole) of 4-[4-(α-hydroxy-α-phenylbenzyl)piperidino]-1-(2-thienyl)butan-1-one hydrochloride, 500 ml of isopropyl alcohol and 500 ml of concentrated HCl was heated on a steam bath for 3 hours, and the solvent was removed under vacuum. Isopropyl alcohol and 300 ml of water were added to the residue and heated to 80° C. Upon cooling a precipitate formed which was collected and recrystallized from methanol-ethyl acetate and toluene to give the desired product, M.P. 132.5°-134.5° C.

EXAMPLE 6

4-[4-(Diphenylmethylene)piperidino]butyrophenone hydrochloride

To 22.5 g (0.05 mole) of 4-[4-(α-hydroxy-α-phenylbenzyl)piperidino]butyrophenone hydrochloride in 300 ml of butanone was added 200 ml of concentrated HCl. The mixture was refluxed with stirring for 2 hours then allowed to stir overnight at room temperature. The mixture was refluxed with stirring an additional 2 hours after which the solvent was removed. The remaining residue was recrystallized from butanone and butanone-diethyl ether to give the desired product, M.P. 160°-161.5° C.

EXAMPLE 7

1-[4-(p-tert-Butylphenyl)-3-butenyl]-4-(diphenylmethylene)-piperidine hydrochloride A mixture of 63.4 g (0.134 mole) of α-(p-tert-butylphenyl)-4-(α-hydroxy-α-phenylbenzyl)-1-piperidinebutanol hydrochloride, 400 ml of 37% HCl, and 250 ml of butanone was refluxed under a nitrogen atmosphere for 17 hours. The solvent and excess acid were removed under vacuum. The mixture was extracted into toluene, and a precipitate formed upon addition of ether. After cooling, the precipitate was collected by filtration, washed with ether and recrystallized from ethyl acetate to give the desired product, M.P. 224°-231° C.

EXAMPLE 8

4'-Bromo-4-[4-(diphenylmethylene)piperidino]-butyrophenone hydrochloride

A mixture of 20 g (0.038 mole) of 4'-bromo-4-[4-(α-hydroxy-α-phenylbenzyl)piperidino]butyrophenone hydrochloride, 500 ml of 37% HCl and 250 ml of n-butanol was refluxed for 3 hours after which the solvent and excess acid were removed under vacuum. The remaining residue was recrystallized from isopropyl alcohol to give the desired product, M.P. 228°-230° C.

EXAMPLE 9

4'-tert-Butyl-4-[4-(diphenylmethylene)piperidino]-butyrophenone hydrochloride

A mixture of 30 g (0.059 mole) of 4'-tert-butyl-4-[4-(α-hydroxy-α-phenylbenzyl)piperidino]butyrophenone, 400 ml of 37% HCl, 200 ml of water and 100 ml of n-butanol was refluxed for one and one-half hours after which the solvent and excess acid were removed. The remaining residue was recrystallized from toluene to give the desired product, M.P. 223.5°–225.5° C.

EXAMPLE 10

1-[4-(p-Bromophenyl)-3-butenyl]-4-(diphenylmethylene)-piperidine hydrochloride

A mixture of 10 g (0.02 mole) of α-(p-bromophenyl)-4-(α-hydroxy-α-phenylbenzyl)-1-piperidinebutanol, 150 ml of concentrated HCl, 150 ml of water and 50 ml of n-butanol was heated for 2 hours at reflux. The solvent was removed under vacuum, and the remaining residue was recrystallized from ethyl acetate to give the desired product, M.P. 215°–217° C. Alternatively, the title compound may be prepared by a similar acid dehydration reaction of α-(p-bromophenyl)-4-(diphenylmethylene)-1-(piperidinebutanol hydrochloride, M.P. 215°–217° C.

EXAMPLE 11

4'-Fluoro-4-[4-(diphenylmethylene)piperidino]-butyrophenone

A mixture of 99.9 g (0.4 mole) of 4-(diphenylmethylene)piperidine, 88 g (0.44 mole) of 4-chloro-4'-fluorobutyrophenone, 64.0 g (0.64 mole) of potassium bicarbonate, and a small amount of potassium iodide in 1500 ml of toluene was refluxed for 5 days. The reaction mixture was filtered and the filtrate was concentrated at reduced pressure leaving a residue which was dissolved in about 800 ml of ethyl acetate. This solution was concentrated to about 500 ml and allowed to stand for one day. The resulting precipitate was recrystallized from methanol-ethyl acetate, made basic with sodium hydroxide solution, water washed, and the product recrystallized from petroleum-ether to give the title compound, M.P. 111°–114° C.

EXAMPLE 12

An illustrative composition for hard gelatin capsules is as follows:

| | |
|---|---|
| (a) 4-[4-(diphenylmethylene)-1-piperidyl]-1-(2-thienyl)-1-butanone hydrochloride | 10 mg |
| (b) talc | 5 mg |
| (c) lactose | 100 mg |

The formulation prepared by passing the dry powders of (a) and (b) through a fine mesh screen and mixing them well. The powder is then filled into hard gelatin capsules at a net fill of 115 mg per capsule.

EXAMPLE 13

An illustrative composition for tablets is as follows:

| | |
|---|---|
| (a) 4'-tert-butyl-4-[4-(diphenylmethylene)-piperidino]butyrophenone | 5 mg |
| (b) starch | 43 mg |
| (c) lactose | 60 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 14

An illustrative composition for an aerosol solution is the following:

| | Weight percent |
|---|---|
| (a) 4'-tert-butyl-4-[4-(diphenylmethylene)piperidino]butyrophenone | 5.0 |
| (b) ethanol | 35.0 |
| (c) dichlorodifluoromethane | 60.0 |

The materials (a), (b) and (c) are packaged in 15 ml stainless steel containers equipped with a metering valve designed to meter 0.2 grams per dose, an equivalent of 10 mg of novel compound (a).

EXAMPLE 15

An illustrative composition for an injectable suspension is the following 1 ml ampul for an intramuscular injection.

| | Weight percent |
|---|---|
| (a) 4-(diphenylmethyl)-1-[4-(p-fluorophenyl)-3-butenyl]piperidine hydrochloride (particle size <10μ) | 1.0 |
| (b) polyvinylpyrrolidone (M.W. 25000) | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 16

An illustrative composition for an aerosol suspension is the following:

| | Weight percent |
|---|---|
| (a) 1-[4-phenyl-4-butenyl]-4-(diphenylmethyl)piperidine hydrochloride (particle size <10μ) | 20.0 |
| (b) sorbitan trioleate | 0.5 |
| (c) dichlorodifluoromethane | 39.75 |
| (d) dichlorodifluoroethane | 39.75 |

The materials (a)–(d) are packaged in 15 ml stainless steel containers equipped with a metering valve designed to meter 50 mg per dose, an equivalent of 10 mg of novel compound (a).

EXAMPLE 17

4-[4-(Diphenylmethylene)piperidino]-4'-methoxybutyrophenone hydrochloride

By the procedure of Example 3 only substituting for 4'-fluoro-4-[4-(α-hydroxy-α-phenylbenzyl)piperidino]-butyrophenone hydrochloride an appropriate amount of 4-[4-(α-hydroxy-α-phenylbenzyl)piperidino]-4'-methoxybutyrophenone hydrochloride, the desired product was obtained upon recrystallization from methanol-benzene, M.P. 185.5°–187° C.

EXAMPLE 18

4'-Dimethylamino-4-[4-(diphenylmethylene)-piperidino]butyrophenone

A mixture of 3 g (0.0065 mole) of 4'-dimethylamino-4-[4-(α-hydroxy-α-phenylbenzyl)piperidino]butyrophenone hydrochloride, 150 ml of ethanol and 150 ml of 37% HCl was heated on a steam bath about 4 hours. The solvent and excess acid were removed. The remaining solid was recrystallized from methanol-butanone, converted to the free base, and recrystallized for benzene-hexane to give the desired product, M.P. 110°–112° C.

We claim:

1. A method of treating the symptoms of an allergic reaction in a patient comprising administering to said patient from about 0.01 to 20 milligrams per kilogram of body weight of the patient of a compound selected from a base of the formula

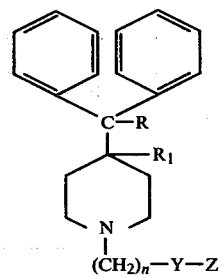

werein R and $R_1$ each represent hydrogen; or R and $R_1$ together from a second bond between the carbon atoms bearing R and $R_1$; n is a positive whole integer of from 1 to 3; Y is selected from the group consisting of —CH=CH— and

with the proviso that when each of R and $R_1$ represents hydrogen, Y represents —CH=CH—, n is equal to 1 or 2; Z is selected from the group consisting of thienyl, phenyl, and substituted phenyl wherein the substituents on the substituted phenyl may be attached at the ortho, meta, or para positions of the substituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, and a saturated monocyclic heterocyclic ring selected from the group consisting of pyrrolidino, piperidino, morpholino and N-(lower)alkylpiperazino; or a pharmaceutically acceptable acid addition salt thereof and a significant amount of a pharmaceutically acceptable carrier.

2. The method of claim 1 wherein Y is

3. A method of inducing bronchial dilation in a patient suffering from bronchial constriction comprising administering to said patient from about 0.01 to 20 milligrams per kilogram of body weight of the patient of a compound selected from a base of the formula

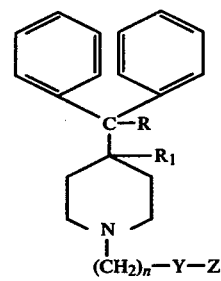

wherein R and $R_1$ each represent hydrogen; or R and $R_1$ together form a second bond between the carbon atoms bearing R and $R_1$; n is a positive whole integer of from 1 to 3; Y is selected from the group consisting of —CH=CH— and

with the proviso that when each of R and $R_1$ represents hydrogen, Y represents —CH=CH—, and when Y represents —CH=CH—, n is equal to 1 or 2; Z is selected from the group consisting of thienyl, phenyl, and substituted phenyl wherein the substituents on the substituted phenyl may be attached at the ortho, meta, or para positions of the substituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrrolidino, piperidino, morpholino and N-(lower)alkylpiperazino; or a pharmaceutically acceptable acid addition salt thereof and a significant amount of a pharmaceutically acceptable carrier.

4. A pharmaceutical composition comprising in unit dosage form from about 1 to 50 milligrams of a compound of the formula

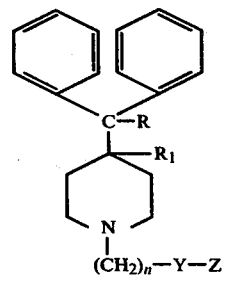

wherein R and $R_1$ each represent hydrogen; or R and $R_1$ together form a second bond between the carbon atoms bearing R and $R_1$; n is a positive whole integer of from 1 to 3; Y is selected from the group consisting of —CH=CH— and

with the proviso that when each of R and $R_1$ represents hydrogen, Y represents —CH=CH—, and when Y represents —CH=CH—, n is equal to 1 or 2; Z is selected from the group consisting of thienyl, phenyl, and substituted phenyl wherein the substituents on the substituted phenyl may be attached at the ortho, meta, or para positions of the substituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, and a saturated monocyclic heterocyclic ring selected from the group consisting of pyrrolidino, piperidino, morpholino and N-(lower)alkylpiperazino; or a pharmaceutically acceptable acid addition salt thereof and a significant amount of a pharmaceutically acceptable carrier.

5. A composition of claim 4 wherein the compound is 4-(diphenylmethyl)-1-(4-phenyl-3-butenyl)piperidine or a pharmaceutically acceptable acid addition salt thereof.

6. A composition of claim 4 wherein the compound is 4-(diphenylmethyl)-1-[4-(p-fluorophenyl)-3-butenyl]-piperidine or a pharmaceutically acceptable acid addition salt thereof.

7. A composition of claim 4 wherein the compound is 4-[4-(diphenylmethylene)piperidino]-4'-fluorobutyrophenone or a pharmaceutically acceptable acid addition salt thereof.

8. A composition of claim 4 wherein the compound is 4-[4-(diphenylmethylene)piperidino]-1-(2-thienyl)-1-butanone or a pharmaceutically acceptable acid addition salt thereof.

9. A composition of claim 4 wherein the compound is 4-[4-(diphenylmethylene)piperidino]butyrophenone or a pharmaceutically acceptable acid addition salt thereof.

10. A composition of claim 4 wherein the compound is 4'-tert-butyl-4-[4-(diphenylmethylene)piperidino]-butyrophenone or a pharmaceutically acceptable acid addition salt thereof.

11. A composition of claim 4 wherein the compound is 4-[4-(diphenylmethylene)piperidino]-4'-methoxybutyrophenone or a pharmaceutically acceptable acid addition salt thereof.

12. The composition of claim 4 wherein Y is

* * * * *